ced by examiner

(12) United States Patent
Stopek et al.

(10) Patent No.: US 8,071,691 B2
(45) Date of Patent: *Dec. 6, 2011

(54) FURANONE ENDCAPPED POLYMERS

(75) Inventors: Joshua B. Stopek, Yalesville, CT (US); Joseph Hotter, Middletown, CT (US); Steve Tsai, Stamford, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 382 days.

This patent is subject to a terminal disclaimer.

(21) Appl. No.: 12/299,705

(22) PCT Filed: May 14, 2007

(86) PCT No.: PCT/US2007/011640
§ 371 (c)(1),
(2), (4) Date: Nov. 5, 2008

(87) PCT Pub. No.: WO2007/133777
PCT Pub. Date: Nov. 22, 2007

(65) Prior Publication Data
US 2009/0318616 A1    Dec. 24, 2009

Related U.S. Application Data

(60) Provisional application No. 60/800,388, filed on May 15, 2006.

(51) Int. Cl.
*C08G 73/02* (2006.01)

(52) U.S. Cl. .................... 525/417; 524/599; 525/419

(58) Field of Classification Search .................. 524/599; 525/417, 419
See application file for complete search history.

(56) References Cited

U.S. PATENT DOCUMENTS

| | | | |
|---|---|---|---|
| 5,718,716 A | 2/1998 | Goddard et al. | |
| 6,485,749 B1 | 11/2002 | Shalaby | |
| 6,548,569 B1 | 4/2003 | Williams et al. | |
| 6,797,743 B2 * | 9/2004 | McDonald et al. | 523/122 |
| 7,064,220 B1 * | 6/2006 | Read et al. | 549/313 |
| 7,851,526 B2 * | 12/2010 | Stopek et al. | 524/111 |

FOREIGN PATENT DOCUMENTS

| | | |
|---|---|---|
| CA | 2328364 A1 | 10/1999 |
| CA | 2495784 A1 | 2/2004 |
| WO | WO 99/54323 A1 | 10/1999 |
| WO | WO 01/76594 A1 | 10/2001 |
| WO | WO 02/00639 A1 | 1/2002 |
| WO | WO 03/084322 A2 | 10/2003 |
| WO | WO 2005/053684 A1 | 6/2005 |
| WO | WO 2007/085042 A1 | 8/2007 |
| WO | WO 2007/133777 A1 | 11/2007 |
| WO | WO 2007/133781 A2 | 11/2007 |

OTHER PUBLICATIONS

Iwasaki, Yasuhiko, et al., "Phosphorylcholine-Containing Polymers for Biomedical Applications", *Analytical and Bioanalytical Chemistry*, vol. 381, pp. 534-546 (2005).
Baveja, J.K., et al., "Biological performance of a novel synthetic furanone-based antimicrobial", *Biomaterials*, vol. 25, pp. 5013-5021 (2004).
Al-Bataineh, Sameer A., et al., "XPS characterization of the surface immobilization of antibacterial furanones", *Surface Science*, vol. 600, pp. 952-962 (2006).
European Search Report from EP Application No. 08 76 9362 mailed Nov. 2, 2010.
European Search Report from EP Application No. 08 76 9360 mailed Nov. 2, 2010.
International Search Report for PCT/US07/11640 date of completion is Sep. 12, 2007 (9 pages).

* cited by examiner

*Primary Examiner* — James J Seidleck
*Assistant Examiner* — Gregory Listvoyb

(57) ABSTRACT

Polymers endcapped with furanones and compositions containing such polymers are suitable for use in making textiles, medical devices, delivery agents, packaging materials, coatings for such items, and the like.

17 Claims, 1 Drawing Sheet

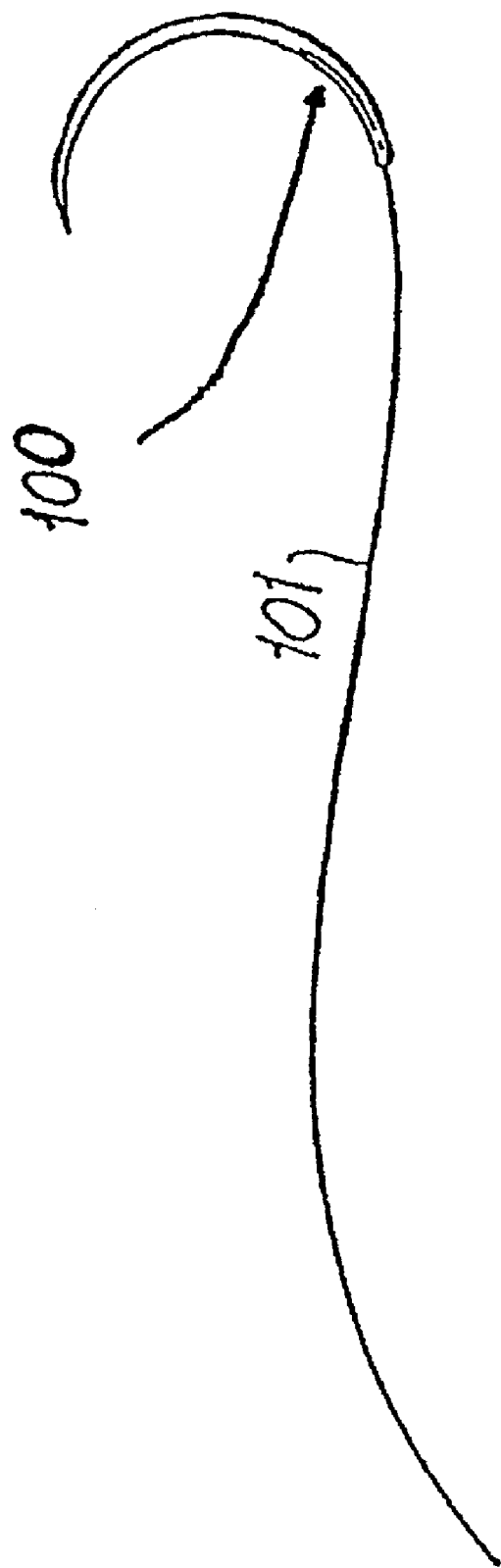

FURANONE ENDCAPPED POLYMERS

CROSS-REFERENCE TO RELATED APPLICATIONS

This application is a National State Application of PCT/US2007/011640 filed May 14, 2007 under 35USC §371 (a), which claims priority of U.S. Provisional Patent Application Ser. No. 60/800,388 filed May 15, 2006, the disclosures of each of the above-identified applications are hereby incorporated by reference in their entirety.

TECHNICAL FIELD

The present disclosure relates to polymers endcapped with furanones, compositions containing such polymers, and articles made from or coated with such polymers or compositions.

BACKGROUND OF RELATED ART

The use of antimicrobial agents on textiles is known. See, e.g., U.S. Patent Application Publication No. 2003/0204916. Antimicrobial agents have also been used within or on medical devices such as sutures and/or packages containing sutures, including the materials utilized to make such items. However, some medical devices may not provide effective levels of antimicrobial activity for a sufficient period of time. Moreover, as is apparent from U.S. Patent Application Publication Nos. 2004/0068293 and 2004/0068294, antimicrobial agents on medical devices can be undesirably transferred to their packages, requiring the use of higher levels of antimicrobial agents in order to obtain the desired antimicrobial effect upon implantation of the suture or other medical device in vivo.

Accordingly, there is a need for medical devices, packaging materials and textiles that can retain enhanced antimicrobial efficacy. There is also a need for an easy and inexpensive method of incorporating or applying antimicrobial agents to a medical device, packaging material or textile that provides protection against microorganisms for extended periods of time, with minimal loss of the antimicrobial agents from the article and/or minimal transference of the antimicrobial agent to packaging materials, etc. In this way, lower amounts of antimicrobial agents may be utilized to achieve the desired antimicrobial effect.

SUMMARY

Furanone endcapped polymers are described. In embodiments, the furanone may be of the formula:

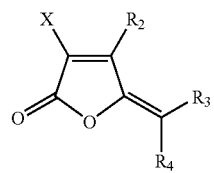

(I)

wherein $R_2$, $R_3$ and $R_4$ are independently or all H, halogen, hydroxyl, or acetate;

"=" represents a double bond; and

X may be a moiety such as H, halogen, formyl, carboxyl, cyano, ester, amide, alkyl, alkoxy, oxoalkyl, alkenyl, alkynyl, aryl or arylalkyl, which moiety may optionally be substituted with one or more substituents; and/or interrupted by one or more hetero atoms; and/or straight chain, branched chain, hydrophobic, hydrophilic or fluorophilic.

In embodiments, polymers endcapped with furanones in accordance with the present disclosure may be formed by the ring opening polymerization of one or more cyclic lactones. In other embodiments, polymers endcapped with furanones in accordance with the present disclosure may include one or more monomers such as lactide, glycolide, trimethylene carbonate, tetramethylene carbonate, dimethyl trimethylene carbonate, dioxanone, dioxepanone, caprolactone, valerolactone, and combinations thereof.

The present disclosure also provides compositions including furanone endcapped polymers of the present disclosure in combination with a component such as an absorbable polymer, a non-absorbable polymer, a fatty acid component, and combinations thereof.

Articles including the furanone endcapped polymers of the present disclosure are also provided. Such articles include, but are not limited to, textiles, packaging materials and medical devices. Coatings including the furanone endcapped polymers of the present disclosure are also provided, as well as articles possessing such coatings.

Methods for endcapping polymers with furanones are also provided. In embodiments, such methods include method endcapping one or more polymers with a furanone and recovering a furanone endcapped polymer. In embodiments, the furanone utilized to endcap the polymer may be of the formula:

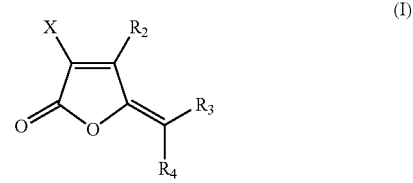

(I)

wherein $R_2$, $R_3$ and $R_4$ are independently or all H, halogen, hydroxyl, or acetate;

"=" represents a double bond; and

X may be a moiety such as H, halogen, formyl, carboxyl, cyano, ester, amide, alkyl, alkoxy, oxoalkyl, alkenyl, alkynyl, aryl or arylalkyl, which moiety may optionally be substituted with one or more substituents; and/or interrupted by one or more hetero atoms; and/or straight chain, branched chain, hydrophobic, hydrophilic or fluorophilic.

The present disclosure also provides sutures including a polymer endcapped with a furanone of the formula:

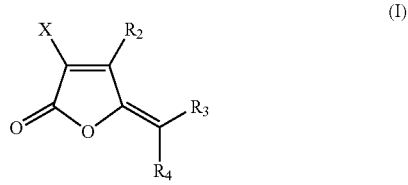

(I)

wherein $R_2$, $R_3$ and $R_4$ are independently or all H, halogen, hydroxyl, or acetate, "=" represents a double bond, and X may be a moiety such as H, halogen, formyl, carboxyl, cyano, ester, amide, alkyl, alkoxy, oxoalkyl, alkenyl, alkynyl, aryl or arylalkyl, which moiety may optionally be substituted with one or more substituents; and/or interrupted by one or more hetero atoms; and/or straight chain, branched chain, hydrophobic, hydrophilic or fluorophilic. In some embodiments, the polymer endcapped with a furanone may be present on at least a portion of a surface of the suture as a coating.

BRIEF DESCRIPTIONS OF THE DRAWINGS

The FIGURE is a depiction of a needled suture in accordance with the present disclosure.

DETAILED DESCRIPTION

The present disclosure provides polymers endcapped with furanones and compositions containing such polymers.

Any polymer may be endcapped in accordance with the present disclosure. The present furanone endcapped polymers may be bioabsorbable or nonabsorbable. In embodiments, a bioabsorbable endcapped polymer may be utilized in a composition of the present disclosure. As used herein the term "polymer" includes homopolymers and copolymers including, but not limited to, random, block or segmented copolymers.

In embodiments, polymers formed by the ring opening polymerization of one or more cyclic lactones may be endcapped with a furanone to form a furanone endcapped polymer of the present disclosure. For example, in embodiments, one or more lactone monomers may be utilized to form the furanone endcapped polymers of the present disclosure. Suitable lactone monomers include, but are not limited to, lactide, glycolide, alkylene carbonates such as trimethylene carbonate, tetramethylene carbonate, and dimethyl trimethylene carbonate, dioxanone, dioxepanone, caprolactone, valerolactone, combinations thereof, and the like.

In embodiments, additional monomers may be added to the lactone monomers thereby forming a copolymer. Monomers which can be copolymerized with the lactones described above include absorbable cyclic amides; absorbable cyclic ether-esters derived from crown ethers; hydroxyacids capable of esterification, including alpha hydroxy acids (such as glycolic acid and lactic acid) and beta hydroxyacids (such as beta hydroxybutyric acid and gamma hydroxyvaleric acid); polyalkyl ethers (such as polyethylene glycol), and combinations thereof.

In embodiments, non-absorbable polymers may be used. Examples of such polymers include, but are not limited to, polyesters, polyamides, polyolefins, halogenated polymers, polyester/polyethers, polyurethanes, homopolymers thereof, copolymers thereof, and combinations thereof.

The polymer to be endcapped can be linear or branched. If the polymer to be endcapped is branched, all, or less than all, of the branches may be endcapped with a furanone.

As noted above, the polymers of the present disclosure may be formed by endcapping one or more polymers with a furanone. Suitable furanones for use in endcapping polymers in accordance with the present disclosure include, for example, compounds of the following formula:

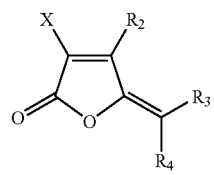

(I)

wherein $R_2$, $R_3$ and $R_4$ are independently or all H, halogen, hydroxyl, or acetate;
"=" represents a double bond; and
X is a moiety such as H, halogen, formyl, carboxyl, cyano, ester, amide, alkyl, alkoxy, oxoalkyl, alkenyl, alkynyl, aryl or arylalkyl, which moiety may optionally be substituted with one or more substituents; and/or interrupted by one or more hetero atoms; and/or straight chain, branched chain, hydrophobic, hydrophilic or fluorophilic. Illustrative examples of suitable furanones include halogenated furanones, hydroxyl furanones, and the like.

As used herein, a substituted furanone or substituted moiety includes one possessing a group such as alkyl, cycloalkyl, alkenyl, alkynyl, halo, haloalkyl, haloalkynyl, hydroxy, alkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenacyl, alkynylacyl, acylamino, diacylamino, acyloxy, alkylsulfonyloxy, heterocyclyl, heterocycloxy, heterocyclamino, haloheterocyclyl, alkylsulfenyl, carboalkoxy, alkylthio, acylthio, and/or phosphorus-containing groups such as phosphono and phosphinyl.

As used herein, "alkyl", used either alone or in compound words such as "haloalkyl" or "alkylthio", includes straight chain or branched $C_{1-12}$ alkyl groups. Examples include methyl, ethyl, propyl, isopropyl and the like.

As used herein, "alkoxy" includes straight chain or branched alkoxy, in embodiments $C_{1-12}$ alkoxy such as methoxy, ethoxy, n-propoxy, isopropoxy and butoxy isomers.

As used herein, "alkenyl" includes groups formed from straight chain, branched or mono- or polycyclic alkenes including ethylenically mono- or poly-unsaturated alkyl or cycloalkyl groups as previously defined, in embodiments $C_{2-12}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4, pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, or 1,3,5,7-cyclooctatetraenyl.

As used herein, "halogen" and/or "halogenated" includes fluorine, chlorine, bromine and/or iodine.

As used herein, "heteroatoms" include O, N and/or S.

As used herein, "acyl" used either alone or in compound words such as "acyloxy", "acylthio", "acylamino" or "diacylamino" includes carbamoyl, aliphatic acyl groups and acyl groups containing a heterocyclic ring which may be referred to as heterocyclic acyl, in embodiments $C_{1-10}$ acyl. Examples of acyl include carbamoyl; straight chain or branched alkanoyl, such as formyl, acetyl, propanoyl, butanoyl, 2-methylpropanoyl, pentanoyl, 2,2-dimethylpropanoyl, hexanoyl, heptanoyl, octanoyl, nonanoyl, decanoyl; alkoxycarbonyl, such as methoxycarbonyl, ethoxycarbonyl, t-butoxycarbonyl, t-pentyloxycarbonyl or heptyloxycarbonyl; cycloalkylcarbonyl such as cyclopopylcarbonyl cyclobutylcarbonyl, cyclopentylcarbonyl or cyclohexylcarbonyl; alkylsulfonyl, such as methylsulfonyl or ethylsulfonyl; alkoxysulfonyl, such as methoxysulfonyl or ethoxysulfonyl; heterocyclylcarbonyl; heterocyclylalkanoyl, such as pyrrolidinylacetyl, pyrrolidinylpropanoyl, pyrrolidinylbutanoyl, pyrrolidinylpentanoyl, pyrrolidinylhexanoyl or thiazolidinylacetyl; heterocyclylalkenoyl, such as heterocyclylpropenoyl, heterocyclylbutenoyl, heterocyclylpentenoyl or heterocyclylhexenoyl; or heterocyclylglyoxyloyl, such as, thiazolidinylglyoxyloyl or pyrrolidinylglyoxyloyl.

As used herein, "fluorophilic" includes the highly attractive interactions certain groups, such as highly fluorinated alkyl groups of $C_4$-$C_{10}$ chain length, have for perfluoroalkanes and perfluoroalkane polymers.

Illustrative examples of suitable furanone endcapping agents include halogenated furanones, hydroxyl furanones, and the like. It should, of course be understood that two or more furanones may be used. In embodiments, specific furanones which may be utilized as an endcapping agent in accordance with the present disclosure include, for example, the following:

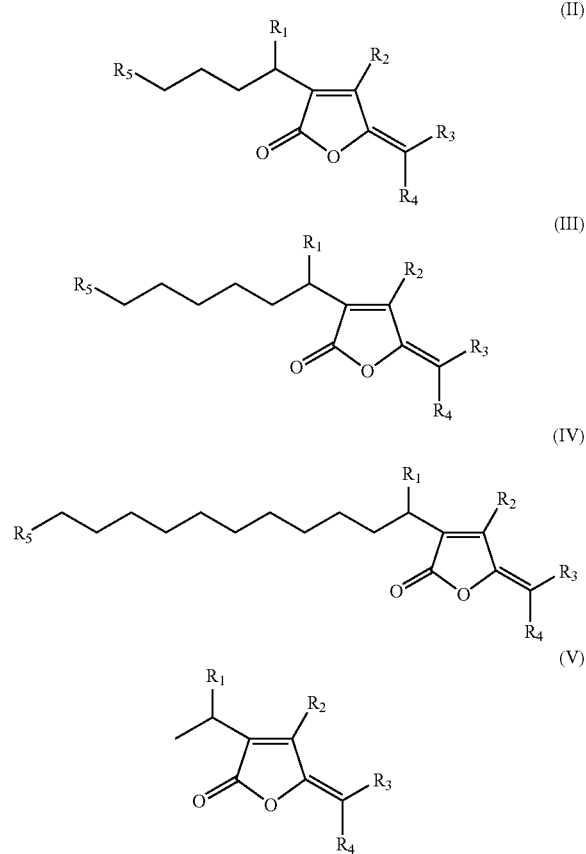

wherein $R_1$, $R_2$, $R_3$, $R_4$ and $R_5$ are independently or all H, halogen, hydroxyl, or acetate.

Halogenated furanones and hydroxyl furanones are known as inhibitors of quorum sensing. Quorum sensing, also known as bacterial signaling, is recognized as a general mechanism for gene regulation in many bacteria, and it allows bacteria to perform in unison such activities as bioluminescence, swarming, biofilm formation, production of proteolytic enzymes, synthesis of antibiotics, development of genetic competence, plasmid conjugal transfer, and spoliation. Quorum sensing is a universal regulatory mechanism used by both Gram-positive bacteria such as *Staphylococcus aureus, Streptococcus pneumoniae, Salmonella enteritidis, Staphylococcus epidermidis, Bacillus subtilis*, and the like, and Gram-negative bacteria such as *Pseudomonas aeruginosa, Escherichia coli, Aeromonas hydrophila*, and the like.

Thus, a quorum sensing inhibitor, such as the halogenated and/or hydroxyl furanones described herein, may act as an antimicrobial agent by inhibiting microbial development and proliferation. In embodiments, a quorum sensing inhibitor may inhibit swarming motility and biofilm formation, both of which frequently underlie the pathophysiology of infectious diseases. The inhibition of swarming and biofilm formation may thus reduce bacterial burden and hence prevent infection and disease progression.

Halogenated and/or hydroxyl furanones may also block quorum sensing and inhibit the growth of bacteria at amounts that are non-toxic to mammalian cells. Given their mechanism of action, halogenated and/or hydroxyl furanones' antipathogenic properties may be effective against a broad spectrum of infectious agents and may be able to reduce and/or prevent colonization of both gram positive and gram negative bacteria, including those noted above.

In addition, unlike antibiotics and antiseptic compounds which kill microbes and carry the risk of inducing antimicrobial resistance, halogenated and/or hydroxyl furanones do not exert such evolutionary pressures. Thus, antimicrobial resistance to an article coated with a composition of the present disclosure possessing a furanone endcapped polymer is not a concern.

Conditions for conducting endcapping are within the purview of those skilled in the art. Endcapping can be achieved by reacting the polymer with a furanone. The conditions under which the polymer is reacted with the furanone may vary widely depending on the specific polymer being endcapped, the specific furanone being employed, and the desired degree of endcapping to be achieved. The amount of furanone employed can be from about 2 to about 8 moles of furanone per mole of polymer. Suitable reaction times and temperatures can be from about 15 minutes to about 72 hours or more at temperatures from about 0° C. to about 250° C.

Articles prepared from or coated with a composition containing a furanone endcapped polymer of the present disclosure may display improved resistance to bacteria. The furanone endcapped polymers thus produced have a furanone attached via a hydrolytically degradable bond to the polymer chain. Advantageously, upon hydrolysis, the present furanone endcapped polymers release low concentrations of the furanone, thus providing antimicrobial activity due to their quorum sensing inhibition to polymers produced therewith.

The present furanone endcapped polymers can be formed into articles using any known technique, such as, for example, extrusion, molding and/or solvent casting. Methods for forming articles with the furanone endcapped polymers of the present disclosure are within the purview of those skilled in the art. The polymers can be used alone or blended with other polymers, either absorbable or non-absorbable.

In embodiments, surgical articles can be manufactured from the furanone endcapped polymers described herein. These include but are not limited to clips and other fasteners, staples, sutures, pins, screws, prosthetic devices, wound dressings, drug delivery devices, anastomosis rings, and other implantable devices.

Fibers can also be made from the present furanone endcapped polymers. In embodiments, fibers made of furanone endcapped polymers of the present disclosure may be knitted or woven with other fibers, either absorbable or non-absorbable fibers to form textiles. The fibers also can be made into non-woven materials to form fabrics, such as meshes and felts.

In some embodiments, compositions in accordance with the present disclosure may be formed by combining the furanone endcapped polymers with other components. In embodiments, compositions including the furanone endcapped polymers can be used as a coating for surgical devices.

For example, in embodiments, coating compositions may contain the present furanone endcapped polymers in combination with a fatty acid component such as a fatty acid, a fatty acid salt, or a salt of a fatty acid ester. Suitable fatty acids may be saturated or unsaturated, and include higher fatty acids having more than about 12 carbon atoms. Suitable saturated fatty acids include, for example, stearic acid, palmitic acid, myristic acid and lauric acid. Suitable unsaturated fatty acids include oleic acid, linoleic acid, and linolenic acid. In addition, an ester of fatty acids, such as sorbitan tristearate or hydrogenated castor oil, may be used.

Suitable fatty acid salts include the polyvalent metal ion salts of $C_6$ and higher fatty acids, in embodiments those having from about 12 to about 22 carbon atoms, and mixtures thereof. Fatty acid salts including the calcium, magnesium, barium, aluminum, and zinc salts of stearic, palmitic and oleic acids may be useful in some embodiments of the present disclosure. Some useful salts include commercial "food grade" calcium stearate which contains a mixture of about one-third $C_{16}$ and two-thirds $C_{18}$ fatty acids, with small amounts of the $C_{14}$ and $C_{22}$ fatty acids.

Suitable salts of fatty acid esters which may be included in the compositions of the present disclosure include calcium, magnesium, aluminum, barium, or zinc stearoyl lactylate; calcium, magnesium, aluminum, barium, or zinc palmityl lactylate; and/or calcium, magnesium, aluminum, barium, or zinc olelyl lactylate. In embodiments; calcium stearoyl-2-lactylate (such as the calcium stearoyl-2-lactylate commercially available under the tradename VERV from American Ingredients Co., Kansas City, Mo.) may be utilized. Other fatty acid ester salts which may be utilized include lithium stearoyl lactylate, potassium stearoyl lactylate, rubidium stearoyl lactylate, cesium stearoyl lactylate, francium stearoyl lactylate, sodium palmityl lactylate, lithium palmityl lactylate, potassium palmityl lactylate, rubidium palmityl lactylate, cesium palmityl lactylate, francium palmityl lactylate, sodium olelyl lactylate, lithium olelyl lactylate, potassium olelyl lactylate, rubidium olelyl lactylate, cesium olelyl lactylate, and francium olelyl lactylate.

Where utilized, the amount of fatty acid component can be from about 5 percent to about 60 percent by weight of the total composition. In embodiments, the fatty acid component may be present in an amount from about 15 percent to about 55 percent by weight of the total composition.

In one embodiment, the furanone endcapped polymer can be present in an amount from about 45 to about 60 weight percent of the composition and the fatty acid component, such as a fatty acid salt or a salt of a fatty acid ester, can be present in an amount from about 40 to about 55 weight percent of the composition. In embodiments, the furanone endcapped polymer can be present in an amount from about 50 to about 55 weight percent of the composition and the fatty acid component can be present in an amount from about 45 to about 50 weight percent of the composition.

In other embodiments, the furanone endcapped polymers of the present disclosure may be combined with additional polymeric materials, such as oligomers and/or polymers. The additional polymeric materials can be absorbable or non-absorbable. The additional polymeric materials may be blended with or bonded to (e.g., to create a block copolymer) the furanone endcapped polymers of the present disclosure.

Bioabsorbable polymers which may be utilized in compositions of the present disclosure are within the purview of those skilled in the art and include those containing linkages derived from monomers including, for example, glycolide, lactide, glycolic acid, lactic acid, caprolactone, trimethylene carbonate, dioxanones, dioxepanones, and the like, and homopolymers, copolymers and combinations thereof.

In other embodiments, the furanone endcapped polymers of the present disclosure may be combined with polyalkylene oxides such as polyethylene oxides, polyethylene glycol, polypropylene glycol, and the like. Such combinations may include blends or copolymers of the furanone endcapped polymers of the present disclosure with the polyalkylene oxide oligomers or polymers. The resulting composition may thus possess antimicrobial properties due to the presence of the furanone endcapped polymers described above.

Furanone endcapped polymers of the present disclosure may be combined with combinations of the foregoing components, e.g., fatty acid components, absorbable components, non-absorbable components, and the like, to form compositions of the present disclosure.

Packaging materials which may formed with the compositions of the present disclosure include packaging for products such as medical devices, pharmaceuticals, textiles, consumer goods, foods, and the like. Packing materials may be formed of any suitable material within the purview of those skilled in the art.

Compositions including these furanone endcapped polymers can also be used as coatings on textiles, packaging materials, and medical devices as noted above.

Textiles which may be coated with coatings of the present disclosure include fibers made of furanone endcapped polymers of the present disclosure, as well as other natural fibers, synthetic fibers, blends of natural fibers, blends of synthetic fibers, and blends of natural fibers with synthetic fibers. Suitable other materials utilized to form textiles include polyesters, polyamides, polyolefins, halogenated polymers, polyester/polyethers, polyurethanes, homopolymers thereof, copolymers thereof, and combinations thereof. Specific examples of suitable materials include polyethylene, polypropylene, polybutylene, polyvinyl chloride, polyethylene terephthalate, nylon 6, and nylon 6,6.

Medical devices possessing a coating of the present disclosure may be formed of furanone endcapped polymers of the present disclosure. In embodiments, medical devices can also be formed of absorbable materials, nonabsorbable materials, and combinations thereof. Suitable absorbable materials which may be utilized to form the medical device include trimethylene carbonate, caprolactone, dioxanone, glycolic acid, lactic acid, glycolide, lactide, homopolymers thereof, copolymers thereof, and combinations thereof. Suitable non-absorbable materials which may be utilized to form the medical device include polyolefins, such as polyethylene, polypropylene, copolymers of polyethylene and polypropylene, and blends of polyethylene and polypropylene.

As noted above, furanone endcapped polymers of the present disclosure may also be used to form coatings for articles, including textiles, medical devices, and packaging materials. In embodiments, the coating of the present disclosure can be applied as a solution and the solvent evaporated to leave the coating components, in embodiments, the furanone endcapped polymer. Suitable solvents which may be utilized in forming the solution include any solvent or combination of solvents suitable for the chosen coating composition. To be suitable, the solvent should (1) be miscible with the coating components including the furanone endcapped polymer, and (2) not appreciably affect the integrity of any material used to form the article being coated, such as a suture. Some examples of suitable solvents include alcohols, ketones, ethers, aldehydes, acetonitrile, acetic acid, methylene chloride, chloroform and water. In embodiments, methylene chloride may be used as a solvent.

Preparing a coating solution of the present disclosure is also a relatively simple procedure and can be accomplished by blending, mixing, and the like. In one embodiment, where a furanone endcapped polymer and methylene chloride are utilized to form the coating solution, the desired amount of furanone endcapped polymer is placed into a container, followed by the addition of the desired amount of methylene chloride. The two ingredients may then be mixed thoroughly to combine the ingredients. In embodiments, a fatty acid component as described above, including a calcium stearoyl lactate, may be included in the coating solution.

Any known technique may be employed for applying the coating, for example as a solution or suspension, to an article. Suitable techniques include dipping, spraying, wiping and brushing. The article wetted with the coating solution or suspension may be subsequently passed through or held in a drying oven for a time and at a temperature sufficient to vaporize and drive off the solvent.

In one embodiment, a medical device in accordance with the present disclosure may be a suture. Sutures in accordance with the present disclosure may be monofilament or multifilament and may be made of any conventional material, including both bioabsorbable and non-bioabsorbable materials, such as surgical gut, silk, cotton, polyolefins such as polypropylene, polyamides, polyglycolic acids, polyesters such as polyethylene terephthalate and glycolide-lactide copolymers, etc.

In one embodiment, the suture may be made of a polyolefin. Suitable polyolefins include polyethylene, polypropylene, copolymers of polyethylene and polypropylene, and blends of polyethylene and polypropylene. In some embodiments, polypropylene can be utilized to form the suture. The polypropylene can be isotactic polypropylene or a mixture of isotactic and syndiotactic or atactic polypropylene.

In other embodiments, the suture may be made from synthetic absorbable polymers such as those made from glycolide, lactide, caprolactone, alkylene carbonates (i.e., trimethylene carbonate, tetramethylene carbonate, etc.), dioxanones, and copolymers and combinations thereof. One combination which may be utilized includes glycolide and lactide based polyesters, including copolymers of glycolide and lactide.

As noted above, the suture can be monofilament or multifilament. Where the suture is a monofilament, methods for producing such sutures are within the purview of those skilled in the art. Such methods include forming a suture material, such as a polyolefin resin, and extruding, drawing and annealing the resin to form the monofilament.

Where the sutures are made of multiple filaments, the suture can be made using any technique within the purview of one skilled in the art such as, for example, braiding, weaving or knitting. The filaments may also be combined to produce a non-woven suture. The filaments themselves may be drawn, oriented, crinkled, twisted, comingled or air entangled to form yarns as part of the suture forming process.

In embodiments a multifilament suture of the present disclosure can be produced by braiding. The braiding can be done by any method within the purview of those skilled in the art. For example, braid constructions for sutures and other medical devices are described in U.S. Pat. Nos. 5,019,093, 5,059,213, 5,133,738, 5,181,923, 5,226,912, 5,261,886, 5,306,289, 5,318,575, 5,370,031, 5,383,387, 5,662,682, 5,667,528, and U.S. Pat. No. 6,203,564, the entire disclosures of each of which are incorporated by reference herein. Once the suture is constructed, it can be sterilized by any means within the purview of those skilled in the art.

In some cases a tubular braid, or sheath, can be constructed about a core structure which is fed through the center of a braider. Known tubular braided sutures, including those possessing cores, are disclosed, e.g., in U.S. Pat. Nos. 3,187,752, 3,565,077, 4,014,973, 4,043,344, and U.S. Pat. No. 4,047,533.

Medical devices and packaging materials in accordance with this disclosure can be sterilized in accordance with techniques within the purview of those skilled in the art.

If desired, in addition to the furanone endcapped polymers of the present disclosure, compositions described herein can optionally contain additional components, e.g., dyes, antimicrobial agents, growth factors, anti-inflammatory agents, and the like. The term "antimicrobial agent" as used in the present disclosure includes antibiotics, antiseptics, disinfectants and combinations thereof. In embodiments, the antimicrobial agent may be an antiseptic, such as triclosan or one of the furanones described above.

Classes of antibiotics that can be combined with the furanone endcapped polymers include tetracyclines like minocycline; rifamycins like rifampin; macrolides like erythromycin; penicillins like nafcillin; cephalosporins like cefazolin; beta-lactam antibiotics like imipenem and aztreonam; aminoglycosides like gentamicin and TOBRAMYCIN®; chloramphenicol; sulfonamides like sulfamethoxazole; glycopeptides like vancomycin; quinolones like ciprofloxacin; fusidic acid; trimethoprim; metronidazole; clindamycin; mupirocin; polyenes like amphotericin B; azoles like fluconazole; and beta-lactam inhibitors like sulbactam.

Examples of antiseptics and disinfectants which may be combined with the furanone endcapped polymers include hexachlorophene; cationic biguanides like chlorhexidine and cyclohexidine; iodine and iodophores like povidone-iodine; halo-substituted phenolic compounds like PCMX (i.e., p-chloro-m-xylenol) and triclosan (i.e., 2,4,4'-trichloro-2'hydroxy-diphenylether); furan medical preparations like nitrofurantoin and nitrofurazone; methenamine; aldehydes like glutaraldehyde and formaldehyde; and alcohols. In some embodiments, at least one of the antimicrobial agents may be an antiseptic, such as triclosan.

The furanone endcapped polymers of the present disclosure may be combined with various optional ingredients, such as stabilizing agents, thickeners, colors, etc. The optional ingredients may represent up to about 10% of the total weight of the compositions formed with furanone endcapped polymers of the present disclosure.

As low amounts of furanones are required in compositions of the present disclosure, existing formulations and manufacturing processes need only minimal modifications to produce the compositions described herein. This ease of formulation and production may reduce both the time and cost necessary to prepare compositions of the present disclosure, compared with adding other antimicrobial agents to existing materials.

In embodiments, a suture in accordance with the present disclosure may be attached to any surgical needle within the purview of those skilled in the art to produce a needled suture. Such a needled suture is depicted in the FIGURE, with suture 101 attached to needle 100. Wounds may be sutured by passing a needled suture through tissue to create wound closure. The needle may then be removed from the suture and the suture tied. The suture may remain in the tissue and help prevent contamination and infection of said tissue by virtue of its antimicrobial properties, thereby promoting wound healing and minimizing infection. The suture coating also advantageously enhances the surgeon's ability to pass the suture through tissue, and increases the ease and security with which he/she can tie the suture.

While the above description contains many specifics, these specifics should not be construed as limitations on the scope of the disclosure herein but merely as exemplifications of particularly useful embodiments thereof. Those skilled in the art will envision many other possibilities within the scope and spirit of the disclosure as defined by the claims appended hereto.

What is claimed is:

1. A furanone endcapped polymer comprising a polymer comprising one or more monomers selected from the group consisting of lactide, glycolide, trimethylene carbonate, tetramethylene carbonate, dimethyl trimethylene carbonate, dioxanone, dioxepanone, caprolactone, valerolactone, and combinations thereof, endcapped with a furanone of the formula:

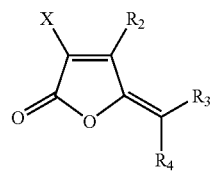
(I)

wherein $R_2$, $R_3$ and $R_4$ are independently or all H, halogen, hydroxyl, or acetate, "═" represents a double bond, and X is a moiety selected from the group consisting of H, halogen, formyl, carboxyl, cyano, ester, amide, alkyl, alkoxy, oxoalkyl, alkenyl, alkynyl, aryl or arylalkyl, which moiety may optionally be substituted with one or more substituents or interrupted by one or more hetero atoms.

2. The furanone endcapped polymer of claim 1, wherein the furanone is of the formula:

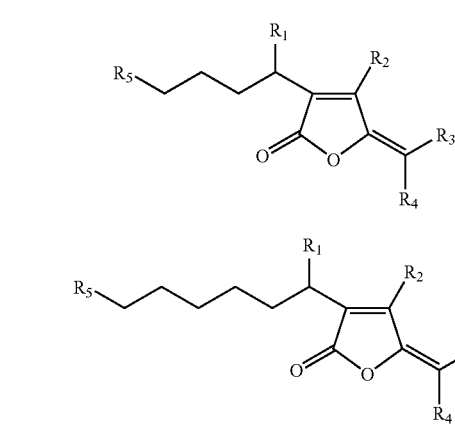
(II)

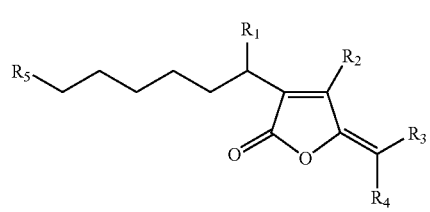
(III)

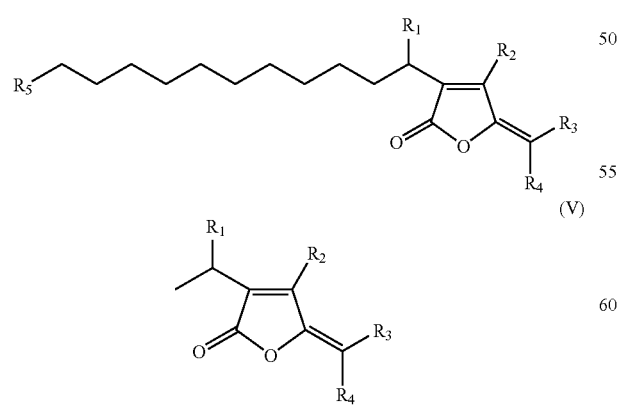
(IV)

(V)

wherein $R_1$, $R_2$, $R_3$, $R_4$ and $R_5$ are independently or all H, halogen, hydroxyl, or acetate.

3. An article comprising the furanone endcapped polymer of claim 1.

4. The article of claim 3, wherein the article is selected from the group consisting of textiles, packaging materials and medical devices.

5. A coating comprising the furanone endcapped polymer of claim 1.

6. A composition comprising the furanone endcapped polymer of claim 1 in combination with a component selected from the group consisting of absorbable polymers, non-absorbable polymers, fatty acid components, and combinations thereof.

7. An article comprising the composition of claim 6.

8. The article of claim 7, wherein the article is selected from the group consisting of textiles, packaging materials and medical devices.

9. A coating comprising the composition of claim 6.

10. A method comprising:

endcapping one or more polymers comprising one or more monomers selected from the group consisting of lactide, glycolide, trimethylene carbonate, tetramethylene carbonate, dimethyl trimethylene carbonate, dioxanone, dioxepanone, caprolactone, valerolactone, and combinations thereof with a furanone of the formula:

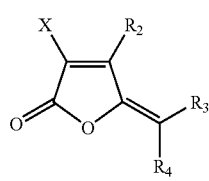
(I)

wherein $R_2$, $R_3$ and $R_4$ are independently or all H, halogen, hydroxyl, or acetate, "═" represents a double bond, and X is a moiety selected from the group consisting of H, halogen, formyl, carboxyl, cyano, ester, amide, alkyl, alkoxy, oxoalkyl, alkenyl, alkynyl, aryl or arylalkyl, which moiety may optionally be substituted with one or more substituents or interrupted by one or more hetero atoms; and recovering a furanone endcapped polymer.

11. The method of claim 10, wherein the furanone is of the formula:

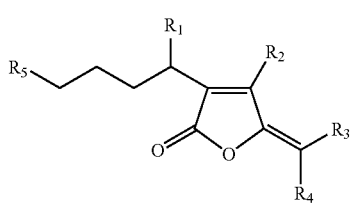
(II)

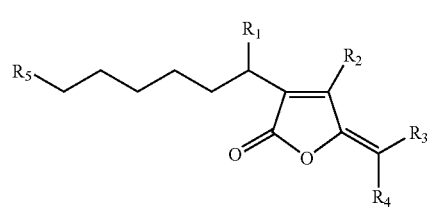
(III)

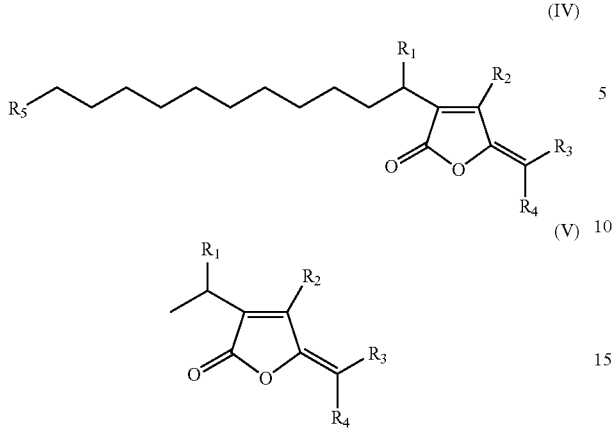

wherein $R_1$, $R_2$, $R_3$, $R_4$ and $R_5$ are independently or all H, halogen, hydroxyl, or acetate.

12. The method of claim 10, wherein the furanone can be in an amount from about 2 to about 8 moles of furanone per mole of polymer.

13. The method of claim 10, wherein the endcapping of one or more polymers with a furanone occurs for a period of time from about 15 minutes to about 72 hours, at a temperature from about 0° C. to about 250° C.

14. A suture comprising a polymer comprising one or more monomers selected from the group consisting of lactide, glycolide, trimethylene carbonate, tetramethylene carbonate, dimethyl trimethylene carbonate, dioxanone, dioxepanone, caprolactone, valerolactone, and combinations thereof endcapped with a furanone of the formula:

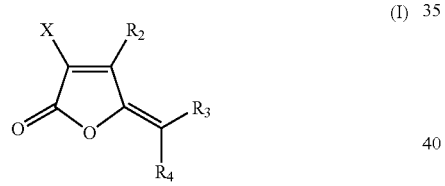

wherein $R_2$, $R_3$ and $R_4$ are independently or all H, halogen, hydroxyl, or acetate, "⸺" represents a double bond, and X is a moiety selected from the group consisting of H, halogen, formyl, carboxyl, cyano, ester, amide, alkyl, alkoxy, oxoalkyl, alkenyl, alkynyl, aryl or arylalkyl, which moiety may optionally be substituted with one or more substituents or interrupted by one or more hetero atoms.

15. The suture of claim 14, wherein the polymer comprises one or more monomers selected from the group consisting of lactide, glycolide, trimethylene carbonate, tetramethylene carbonate, dimethyl trimethylene carbonate, dioxanone, dioxepanone, caprolactone, valerolactone, and combinations thereof.

16. The suture of claim 14, wherein the furanone is of the formula:

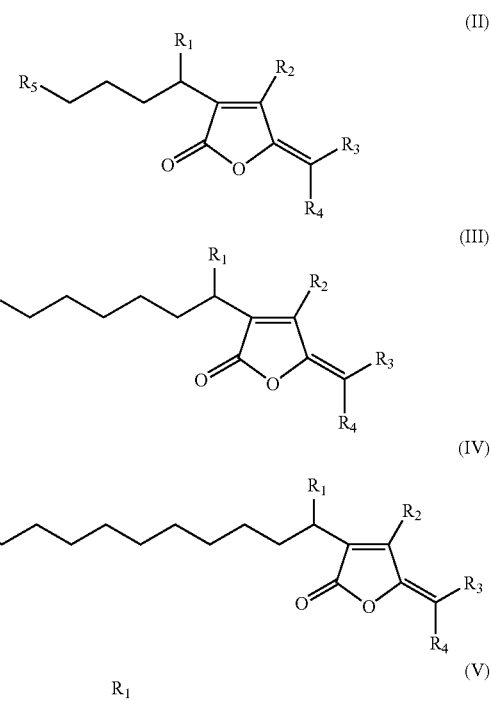

wherein $R_1$, $R_2$, $R_3$, $R_4$ and $R_5$ are independently or all H, halogen, hydroxyl, or acetate.

17. The suture of claim 14, wherein at least a portion of a surface of the suture possesses a coating comprising the polymer endcapped with a furanone.

* * * * *